United States Patent [19]

Sharpe

[11] Patent Number: 5,554,537
[45] Date of Patent: Sep. 10, 1996

[54] NON-DESTRUCTIVE SURFACE SAMPLER

[75] Inventor: Anthony N. Sharpe, Almonte, Canada

[73] Assignee: Her Majesty the Queen in right of Canada as represented by the Minister of Health and Welfare Canada, Ottawa, Canada

[21] Appl. No.: 563,976

[22] Filed: Nov. 29, 1995

[51] Int. Cl.⁶ .................................................. C12M 1/26
[52] U.S. Cl. ........................................ 435/309.1; 435/30
[58] Field of Search ................................. 435/30, 309.1; 422/99; 15/320

[56] References Cited

U.S. PATENT DOCUMENTS 4,281,066  7/1981  Thran et al. ............................ 435/292
4,945,921  8/1990  Okimoto ................................. 128/759

Primary Examiner—David A. Redding
Attorney, Agent, or Firm—Ronald G. Bitner

[57] ABSTRACT

A sampler for determining the microbiological safety or hygienic quality of surfaces comprising a scrubber-retainer which comprises a compressible liquid absorbing elastic element for scrubbing a test surface and releasably retaining a liquid, and a surrounding chamber to confine a region around the scrubber-retainer against the sample surface. The sampler includes a drive mechanism for moving the scrubber-retainer to scrub the test surface and release analytes from the test surface, and alternately compressing and decompressing the compressible material to allow liquid to be alternately released and absorbed, respectively, to produce a suspension of the released analytes.

6 Claims, 2 Drawing Sheets 5,554,537

NON-DESTRUCTIVE SURFACE SAMPLER

FIELD OF THE INVENTION

This invention relates to a surface sampler for determining microbiological safety or hygienic quality.

BACKGROUND OF THE INVENTION

In order to ensure the microbiological safety of foods and clinical environments it is often necessary to sample the surfaces of carcasses, or food manufacturing equipment, or other surfaces, to determine the existence and quantity of microorganisms, or other analytes, such as adenosine triphosphate, thereon. It is usually impractical to measure either microorganisms or hygiene-pertinent analytes directly at a surface because they are very small analytical quantities. Therefore, it is a common practice to remove them from the surface in some way and disperse them in water or other liquid so that they can be measured at a laboratory, for example, by culturing suspended microorganisms. Microorganisms may exist on surfaces in a variety of states. They may be loosely attached to surfaces, in which case they are easily removed; alternatively, they may be adsorbed on the surface or attached in biofilms or trapped in pores, in which case considerably greater effort if required to disperse them. This variability causes problems of reproducibility because usually it is not possible to maintain the suspending liquid and surface in contact with each other long enough to reach an equilibrium.

Many techniques and devices have been developed or proposed with the aim of obtaining representative suspensions of the microorganisms at surfaces, for example, swabbing the surface, shaking the test sample with liquid in a plastic bag, using a liquid spray gun in a sealed container, or by excising a portion of the surface and blending it in a liquid in a blender or other device which disrupts and disperses the microorganisms.

U.S. Pat. No. 4,281,066 to V. Thran, et al, discloses all apparatus for taking samples from surfaces that includes a nozzle for spraying a rinsing liquid atomized by a compressed gas onto the test surface and a container for collecting rinsed-off particles and rinsing liquid. This apparatus requires a compressor and a relatively large quantity of liquid for a small sample area. Also with the arrangement of collector vessel as shown, use is limited to vertical or near vertical surfaces.

None of the prior techniques are entirely satisfactory for a variety of reasons. For example, swabbing is convenient and does not harm the test surface, but is imprecise in its yield of microorganisms; shaking the test sample in a plastic bag is practicable only for small test samples such as chickens; neither shaking nor rinsing with liquid are energetic enough to remove most of the microorganisms; spray techniques are difficult to use when the test sample surface is at angles inclined from the horizontal; and techniques requiring excision destroy the surface and reduce the value of the sample.

There is a need for an analyte suspending device that is simple and inexpensive to operate, non-destructive to the object being tested, that removes a high proportion of bacteria or other analyte from the test surface into liquid suspension, and that call be used on surfaces at any orientation.

SUMMARY OF THE INVENTION

The present invention arose following experiments and observations on the release of microorganisms or other analytes from foods and other surfaces.

It was found that when test samples are rinsed, shaken, or blended in liquid the microbial concentration in suspension usually reaches a plateau, but if the liquid is repeatedly changed and the blending repeated, then more microorganisms are released, until the total number of microorganisms released after several blendings may be much higher than a single suspending indicates. It was discovered that an effect similar to the "Mass Action" effect, known to chemists, controls microbial release, and further, that the volume of liquid used to suspend microorganisms is important, and that for good release the volume should be as high as possible.

While traditional swabs are non-destructive to the test sample and convenient to use, they contain only very small volumes of liquid. It was deduced that the efficiency of traditional swabs at removing microorganisms is low because during swabbing a very high concentration of microorganisms is produced at the swab/sample interface. These microorganisms inhibit the release of further microorganisms because they do not get dispersed through the whole of the liquid but only into a small and variable proportion of it, depending on effects such as the wrist action of the swabber, and this leads to a variable release of microorganisms from the test surface. Similarly previous techniques other than swabs have also not provided for a large enough volume of liquid to be held against the test surface, nor for thorough mixing of released microorganisms into the liquid.

As the result of the above observations and experiments, it was concluded that what was needed was a means to bring surface microorganisms into an equilibrium with a larger volume of liquid than is customary, and that this would need to be done on surfaces at any angle.

The present invention provides a convenient means of presenting a known and relatively large volume of liquid to the test surface, confining this liquid to a defined area of the surface, and maintaining it in contact for a certain period of time to obtain the representative microbial suspension. At the same time the invention applies sufficient and reproducible agitation and scrubbing of the surface so that microorganisms are removed from the test surface and suspended in the liquid without damaging the test surface. Additionally, the invention provides a convenient means to contain the liquid with its suspended microorganisms after removal from the surface so that the suspension does not escape and is easily transportable for analysis.

The present invention provides a surface sampler for microbiological analysis comprising: a scrubber-retainer comprising a compressible liquid absorbing elastic material for scrubbing a test surface and releasably retaining a liquid; a chamber disposed around the scrubber-retainer, said chamber having an open front end to allow the material to contact a test surface, side walls defining a sealing edge for sealing engagement against the test surface, and a rear portion for confining a region around the scrubber-retainer against the test surface to be sampled; and drive means for moving the scrubber-retainer to scrub the test surface and release analytes from the test surface, and for alternately compressing and decompressing the compressible material to allow liquid to be alternately released and absorbed, respectively, to produce a suspension of the released analytes.

BRIEF DESCRIPTION OF THE DRAWINGS

FIGS. 1a and 1b show separable components installed and separated, respectively.

DESCRIPTION OF THE PREFERRED EMBODIMENTS

Figure 1B:
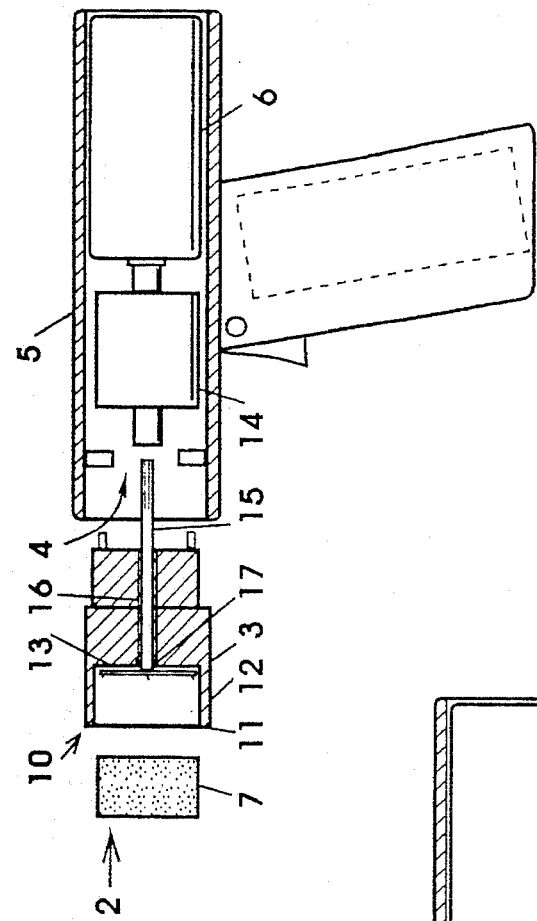
FIGS. 1a and 1b is a schematic illustration of one embodiment of the invention.
Figure 1A:
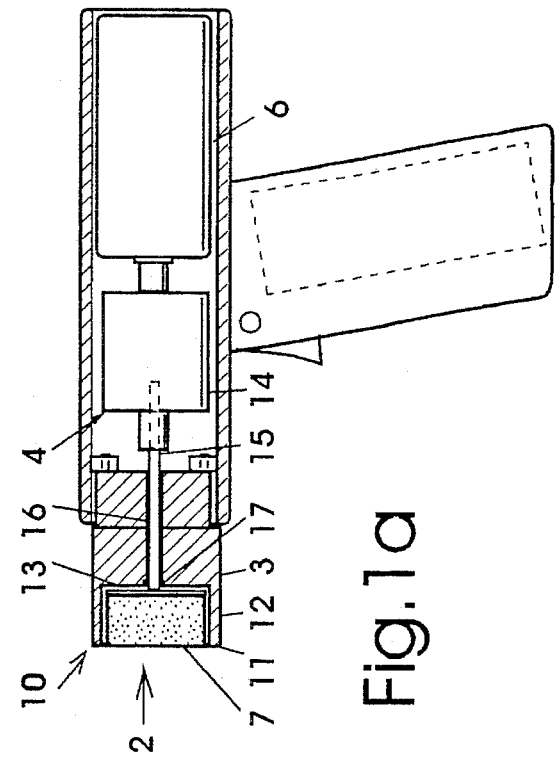

With reference to FIG. 1, the sampler of the present invention comprises a scrubber-retainer 2, a chamber 3, drive means 4, and a suitable housing 5.

The scrubber-retainer 2 comprises a compressible liquid absorbing elastic material 7 for scrubbing a test surface and releasably retaining a liquid. Preferably the compressible liquid absorbing elastic material 7 will be in the form of a porous sponge-like material that is able to retain a relatively large volume of liquid by capillary action, and will release the liquid when compressed and expand to reabsorb liquid when the compressive force is released.

One material found to be suitable for the scrubber-retainer is polyurethane foam having a very open pore structure. This material was found to be suitably elastic, autoclavable and did not adsorb or kill bacteria under short contact times.

It will be understood that the structure of the scrubber-retainer 2 may be modified for a particular application. For example, the scrubber-retainer might be provided with an abrasive surface layer capable of removing analytes which are firmly attached to the test surface.

The scrubber-retainer material 7 may be a separate component removably attached to a support plate 6 by any suitable means, such as by pins or barbs, so that it can be easily removed for analysis after sampling. Alternatively, the material 7 may be more or less permanently attached, for example, as part of a removable disposable assembly.

The scrubber-retainer 2 is disposed within chamber 3 which has an open front end 10 to allow the material 7 to engage a test surface, side walls 12 defining a sealing edge 11 for sealing engagement against the test surface, and a rear closed portion 13 for confining a region around the scrubber-retainer 2 against the test surface to be sampled. In the preferred embodiment, as illustrated, the chamber 3 has a shape similar to that of the scrubber-retainer, which is cylindrical, and with a volume sufficient to accommodate the scrubber-retainer 2 and liquid used and size sufficient to allow the scrubber-retainer 2 to rotate or otherwise move freely. The sealing edge 11 of the side walls 12 may be flexible or rigid depending on the nature of surface to be tested. For example, a flexible sealing edge may be preferred for a rigid and/or uneven surface, while a rigid edge may be adequate for an elastic test surface. Since the vessel is sealed with respect to the sample surface, the operation is not limited to horizontal surfaces but can be performed at any orientation.

The open end 10 of the chamber 3 should have an area suitable for the surface to be tested and will typically be between 10 and 100 cm$^3$. The scrubbing area of the scrubber-retainer will normally be equal to or slightly less than that of the chamber so that it can rotate freely while in the compressed state but easily contact and absorb all free liquid when the apparatus is stopped.

Preferably the chamber 3 will be removably attached to the housing 5, for example by a bayonet fastener, as shown in FIG. 1b. The scrubber-retainer 2 and/or the material 7 will preferably be removable and disposable but cleanable reusable materials are not excluded.

The scrubber-retainer drive means 4 may include any system or mechanism that provides both scrubbing action and compression-decompression motion of the scrubber-retainer 2. Several embodiments of suitable mechanisms are illustrated in FIGS. 2 to 5.

Scrubbing action may be provided by any convenient form of motion of the scrubber-retainer 2 in a plane generally parallel with that of the test surface, and may include rotary, orbital or reciprocating motion. Rotary motion for scrubbing is preferred as it is most easily provided with a rotating motor.

Figure 5:
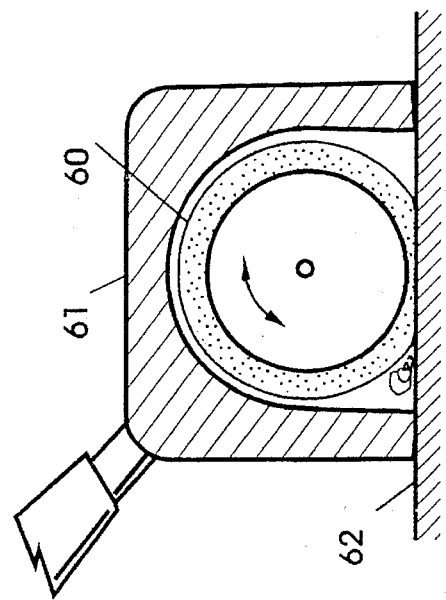
FIG. 5 is a schematic illustration of a portion of another embodiment of the present invention.

Compression and decompression of the compressible material 7 can be conveniently provided by drive means that includes reciprocation, but is not limited thereto. FIG. 5 illustrates an example wherein compression and decompression, as well as the scrubbing, is provided by rotary motion.

The compressive force applied to scrubber-retainer 2 must be high enough to compress it sufficiently that it expels most of its liquid during the compressive stage of the cycle, and also that it scrubs the test surface adequately for analyte release. Typically, the drive mechanism will exert a force of at least 50 g/cm$^2$ on the scrubber-retainer 2 against the test surface, but the force should not be so high that the operator has difficulty holding the sampler against the test surface without leakage, or that the apparatus causes damage to the test surface.

It appears that suitable rotational speeds are in the range between 100 and 1,000 RPM. Further, it appears that 5 to 30 revolutions during each compressive phase are sufficient. Increasing the number of revolutions of the scrubber-retainer beyond a certain point yields diminishing release of analyte from the test surface and delays the distribution of the released analyte into the bulk liquid. The duration of the decompressed stage need only be long enough that expressed liquid can be reabsorbed into the scrubber-retainer, and is typically 0.5 to 3 seconds. For the most rapid sampling, the transition between compressed and decompressed stages, and vice versa, during which little analyte removal occurs, should be as rapid as possible without causing excessive recoil of the sampler.

With reference to FIG. 1, the drive means 4 includes a suitable motor 6 and a mechanism 14 which provides rotary motion to the scrubber-retainer 2, and reciprocating motion for alternately compressing and decompressing the material 7, via output shaft 15. The shaft 15 passes through the rear portion 13 of chamber 3 through an aperture 16 that is provided with a suitable seal 17 to prevent the escape of liquid from the chamber 3.

Preferably the drive means will be controlled in such a manner that the scrubber-retainer material 7 is in a decompressed expanded state when stopped such that liquid and suspended analytes will be contained within the material 7.

For operation, the scrubber-retainer 2 is loaded with liquid in any convenient manner, for example, by pouring the liquid into the chamber containing the scrubber-retainer while the sampler is directed upwards; by immersing or squeezing the scrubber-retainer in a container with the liquid; or by providing pre-filled disposable chambers with scrubber-retainer.

When commencing operation, the scrubber-retainer will be in the retracted or decompressed state so that the sampler can be applied to the test surface at any orientation without spilling liquid.

In operation, the sealing edge 11 of the chamber 3 is pressed against the test surface with sufficient force to prevent leakage of liquid from the chamber in the subsequent procedure. For sampling, the drive means is engaged to produce the scrubbing motion and alternate compression and decompression of the scrubber-retainer material 7.

The scrubbing motion releases microorganism and/or analytes from the test surface, and the alternate compressing and decompressing of the compressible material 7 allows liquid to be alternately released and absorbed, respectively, to mix with the released analytes and produce a suspension.

After the desired amount of scrubbing and mixing is completed, the material 7 is allowed to expand to the decompressed state so that substantially all the liquid with suspended analytes is reabsorbed into the material. At completion of the sampling operation the scrubber-retainer will be in the decompressed state with all the liquid retained in the material. The scrubber-retainer 2 or material 7, containing the liquid with suspended analytes, can then be removed and transported for analysis as desired.

FIG. 2 illustrates one embodiment of a mechanism that provides the necessary alternating compression and decompression as well as rotary motion to the scrubber-retainer 20. Referring to FIG. 2, shaft 21 is connected with a suitable reversible motor (not shown). Shaft 21 is attached to a hollow shaft 22 which, in turn, is attached to lead nut 23. Operatively associated with lead nut 23 is a lead screw 24 which is attached to the output shaft 25. The output shaft 25 has a suitable receiving/support member 26 for the scrubber-retainer material 20. A washer like element 27 has an inner surface 28 adapted to provide some frictional resistance to the rotation of output shaft 25 and also provides a friction surface 29 for engagement by the end of leadscrew 24 during one stage of the operation cycle, as will be described. The moving components are disposed within a suitable fixed housing 30.

Figure 2A:
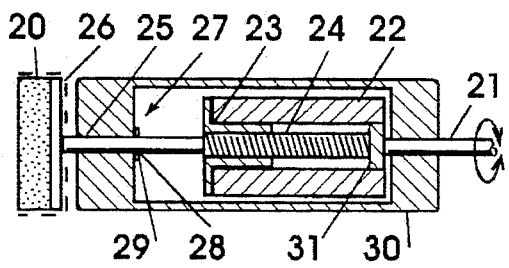
FIGS. 2a, 2b, 3a, 3b, 4a, 4b illustrate embodiments of drive mechanisms for the sampler of the present invention.
Figure 2B:
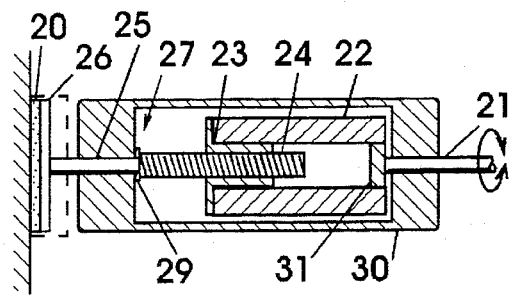

In operation, the shaft 21 will be rotated in alternate directions utilizing a reversible motor controlled by suitable timing means. Operation begins with the leadscrew 24 and attached output shaft 25 in a retracted position, as shown in FIG. 2a. As shaft 21 and 22 is rotated in a counter-clockwise direction, the frictional force exerted by surface 28 on output shaft 25 allows the lead screw 24 to be advanced until it contacts the washer 27, as shown in FIG. 2b, and effects compression of the scrubber-retainer 20 against the test surface. At this point linear motion of the lead screw 24 and output shaft 25 ceases and becomes rotary providing the scrubbing motion of the scrubber-retainer 20. The compressive force exerted on the scrubber-retainer depends on the combined resistance provided by friction surface 28 on shaft 25 and friction between the scrubber-retainer and the test surface that it rotates against. The compression force is limited by the travel limit of the leadscrew 24 upon contact with the washer 27.

After the desired scrubbing action, rotation of the shaft 21 is reversed. From the position shown in FIG. 2b, the lead screw 24 retracts until it contacts the low friction face 31, whereby linear motion ceases and is briefly replaced by rotary motion. At this point the mechanism is again in the position shown in FIG. 2a in preparation for another compression-decompression cycle, or termination of sampling. Upon completion of the desired number of cycles, the scrubber-retainer 20, containing the liquid with suspended analytes, can then be removed and transported for analysis as desired.

Figure 3A:
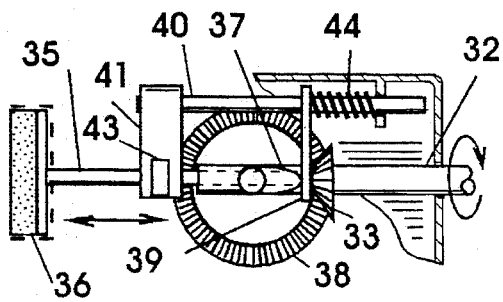
Figure 3B:
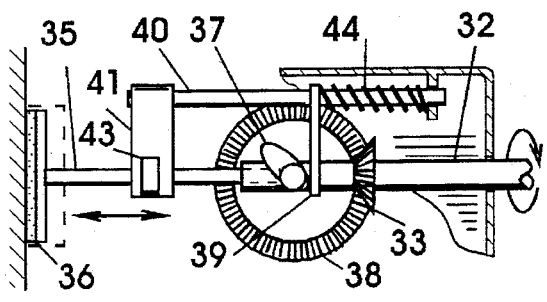

FIG. 3 illustrates another embodiment of a mechanism driven by a motor running continuously in one direction. Referring to FIG. 3, shaft 32 is rotated by a suitable motor (not shown) and has attached thereto bevel gear 33. The shaft 32 includes an internally splined portion for slidably receiving output shaft 35 which provides rotary motion for the scrubber-retainer 36 while allowing reciprocating motion. Reciprocating motion is provided by a mechanism comprising a cam 37 attached to gear 38 which meshes with driving gear 33, and a cam follower 39 which transfers reciprocating motion to output shaft 35 via shaft 40 and yoke 41 which engages a bearing face 43 on output shaft 35. The compression force transmitted to the scrubber-retainer is governed by compression spring 44. It can be seen that the number of revolutions of the shafts 32, or 35, for each compression-decompression cycle is determined by the gear ratio of gear 38 to 33.

Figure 4A:
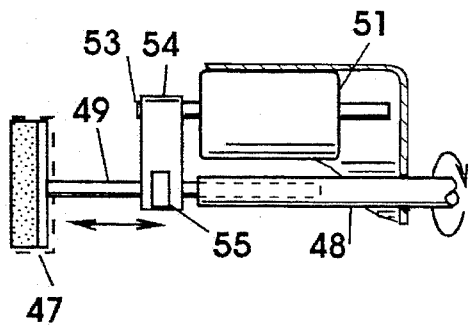
Figure 4B:
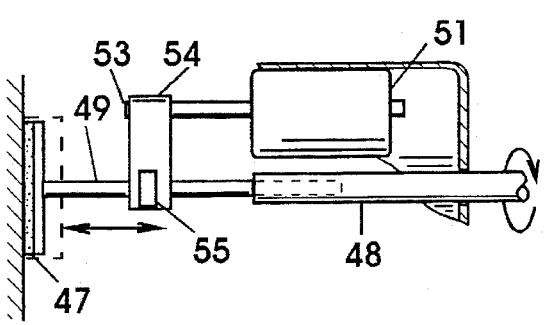

FIG. 4 illustrates another embodiment of a mechanism driven by a motor running continuously in one direction to provide rotary motion for the scrubber-retainer and a linear actuator, such as an electric solenoid or pneumatic cylinder, for compression-decompression of the scrubber-retainer 47. Referring to FIG. 4, shaft 48 is driven by a suitable totally motor (not shown) which is slidably connected to output shaft 49. The linear actuator 51 transfers reciprocating motion to output shaft 49 via shaft 53 and yoke 54 which engages a bearing face 55 on output shaft 49, for compression and decompression of the scrubber-retainer 47. FIG. 4a shows the components with the scrubber-retainer decompressed while FIG. 4b shows the components with the scrubber-retainer compressed. The number of rotations of the shaft 49, or 49, and activation of the linear actuator 51 is controlled with the use of suitable timer means.

FIG. 5 illustrates another embodiment of the invention utilizing rotary motion for both scrubbing and compression-decompression of the scrubber-retainer member. Referring to FIG. 5, the scrubber-retainer 60 is in the form of a cylinder rotatably mounted within a chamber 61 and rotated by a suitable motor (not shown). Scrubbing of the test surface 62 is obtained by the rotary motion of the scrubber-retainer member. Compression of successive portions of the scrubber-retainer 60 is effected as these portions contact the test surface 62, and decompressed as it rotates away from the surface. As portions of the scrubber-retainer are successively compressed and decompressed, liquid is expelled and reabsorbed, respectively, from these portions. Since this arrangement provides compression and decompression on a continuous basis, this embodiment allows the sampler to be drawn over a surface to sample an enlarged surface area.

What is claimed is:

1. A surface sampler for microbiological analysis comprising:

a scrubber-retainer comprising a compressible liquid absorbing elastic material for scrubbing a test surface and releasably retaining a liquid;

a chamber disposed around the scrubber-retainer, said chamber having an open front end to allow the material to contact a test surface, side walls defining a sealing edge for sealing engagement against the test surface, and a rear portion for confining a region around the scrubber-retainer against the test surface to be sampled; and drive means for moving the scrubber-retainer to scrub the test surface and release analytes from the test surface, and alternately compressing and decompressing the compressible material to allow liquid to be alternately released and absorbed, respectively, to produce a suspension of the released analytes.

2. The sampler of claim 1, wherein the scrubber-retainer is rotatably mounted and the drive means rotates the material against the test surface.

3. The device of claim 1, wherein the drive means includes a mechanism for reciprocating the scrubber-retainer for compressing and decompressing the compressible material.

4. The device of claim 3, wherein said mechanism includes means for converting rotary motion to said reciprocating motion for compressing and decompressing the compressible material.

5. The device of claim 1, wherein the drive means includes first drive means for moving the scrubber-retainer to scrub the test surface and release analytes from the test surface, and second drive means for moving the scrubber-retainer for alternately compressing and decompressing the compressible material.

6. The device of claim 1, wherein the drive means includes a shaft which passes through the rear portion of the chamber in sealing engagement therewith.

* * * * *